United States Patent
Ma et al.

(10) Patent No.: US 7,371,904 B2
(45) Date of Patent: May 13, 2008

(54) PROCESSES FOR SYNTHESIS OF 1,3,3,3-TETRAFLUOROPROPENE

(75) Inventors: Jing Ji Ma, West Seneca, NY (US); Sudip Mukhopadhyay, Williamsville, NY (US); Haridasan K. Nair, Williamsville, NY (US); Hsueh S. Tung, Getzville, NY (US); Michael Van Der Puy, Amherst, NY (US)

(73) Assignee: Honeywell International Inc., Morristown, NJ (US)

( * ) Notice: Subject to any disclaimer, the term of this patent is extended or adjusted under 35 U.S.C. 154(b) by 375 days.

(21) Appl. No.: 11/118,504

(22) Filed: Apr. 29, 2005

(65) Prior Publication Data

US 2005/0245774 A1 Nov. 3, 2005

Related U.S. Application Data

(60) Provisional application No. 60/567,426, filed on Apr. 29, 2004, provisional application No. 60/567,429, filed on Apr. 29, 2004.

(51) Int. Cl.
C07C 21/18 (2006.01)
C07C 17/26 (2006.01)
C07C 17/263 (2006.01)
C07C 17/269 (2006.01)

(52) U.S. Cl. .................... 570/136; 570/135; 570/171; 570/172

(58) Field of Classification Search .................. None

See application file for complete search history.

(56) References Cited

U.S. PATENT DOCUMENTS

| | | | |
|---|---|---|---|
| 2,931,840 A | 4/1960 | Marquis | 260/653.3 |
| 3,472,826 A | 10/1969 | Potts et al. | 260/88.2 |
| 4,086,407 A | 4/1978 | Fozzard | 526/75 |
| 5,986,151 A | 11/1999 | Van Der Puy | 570/175 |
| 6,124,510 A | 9/2000 | Elsheikh et al. | 570/156 |
| 6,548,719 B1 | 4/2003 | Nair et al. | 570/157 |
| 2007/0112227 A1 * | 5/2007 | Mukhopadhyay et al. | 570/101 |

FOREIGN PATENT DOCUMENTS

EP WO 01/07384 2/2001

OTHER PUBLICATIONS

Salmon R P Et Al: Chemical and Physical Processes in Combustion, SN, US 1996, pp. 507-510, XP001120412.

* cited by examiner

*Primary Examiner*—Yvonne Eyler
*Assistant Examiner*—Yevgeny Valenrod
(74) *Attorney, Agent, or Firm*—Colleen D. Szuch

(57) ABSTRACT

Disclosed is a process for the synthesis of 1,3,3,3-tetrafluoropropene which comprises, in one embodiment, reacting a compound of $CF_3X^1$ with a compound of $CX^2H=CHX^3$, wherein $X^1$, $X^2$, and $X^3$ are each independently selected from the group consisting of fluorine, chlorine, bromine and iodine, to produce a reaction product comprising a compound of $CF_3CH=CHX^3$, wherein $X^3$ is as described above; and when $X^3$ is not fluorine, fluorinating the compound to produce 1,3,3,3-tetrafluoropropene. The process in another embodiment comprises preparing tetrafluoropropene comprising thermally cracking one or more compounds capable of producing a reaction mixture which preferably comprises diflurocarbene radicals and vinylidene fluoride, and converting said reaction mixture into—tetrafluoropropene (1,3,3,3-tetrafluoropropene).

4 Claims, No Drawings

PROCESSES FOR SYNTHESIS OF 1,3,3,3-TETRAFLUOROPROPENE

FIELD OF THE INVENTION

The present invention relates to methods for the preparation of tetrafluorinated propene. More specifically, this invention concerns processes for the preparation of 1,3,3,3-tetrafluoropropene, $CF_3CH=CHF$, (HFO-1234ze).

BACKGROUND OF THE INVENTION

Tetrafluorpropenes are known to be useful as monomers in the preparation of various homopolymers and copolymers. For example, U.S. Pat. No. 3,472,826 describes tetrafluorpropene as a comonomer in the production of polyethylene. U.S. patent application Ser. No. 10/694,273, which is assigned to the assignee of the present invention, discloses the use of $CF_3CH=CFH$ as a refrigerant with low global warming potential and also as a blowing agent for use in connection with the formation of various types of foams. In addition, $CF_3CH=CFH$ can also be functionalized to variety of compounds useful as intermediates for making industrial chemicals.

Several methods of preparing tetrafluoropropene compounds are known. For example, U.S. Pat. No. 6,548,719 B1 describes generally the production of a wide range of fluoroolefins by dehydrohalogenating, in the presence of a phase transfer catalyst, a compound of formula $CF_3C(R^1{}_aR^2{}_b)C(R^3{}_cR^4{}_d)$ with at least one alkali metal hydroxide, where the R substituents are as defined in the patent, provided that at there is at least one hydrogen and one halogen on adjacent carbon atoms. This patent, while disclosing a process that is efficient and useful for the preparation of numerous tetrafluoropropenes, does not disclose a process specifically for the preparation of 1,3,3,3-tetrafluoropropene.

The preparation of 1,3,3,3-tetrafluoropropene is disclosed in U.S. Pat. No. 5,986,151. This patent discloses a process comprising catalytic dehydrofluorination of $CF_3CH_2CF_2H$ in the gas phase to afford $CF_3CH=CHF$. The preparation of 1,3,3,3-tetrafluoropropene is also disclosed in U.S. Pat. No. 6,124,510. This patent also discloses a process comprising catalytic dehydrofluorination of $CF_3CH_2CF_2H$ in the gas phase. Each of these patents has the disadvantage of being limited by the requirement of isolating 1,1,1,3,3-pentafluoropropane ("245fa") as a starting reactant, which may be undesirable for reasons of cost, availability, and/or otherwise.

Several other methods of preparing tetrafluoropropene compounds are known. For example, U.S. Pat. No. 2,931,840 describes a reaction involving the pyrolysis of methyl chloride with tetrafluoroethylene, or alternatively of methyl chloride with chlorodifluoromethane tetrafluoroethylene. While this patent indicated that this process is capable of producing 2,3,3,3-tetrafluoropropene, there is no indication that the process is effective for producing 1,3,3,3-tetrafluoropropene. In addition, applicants have come to appreciate that the process described in this patent has the disadvantage of requiring in every case the use of methyl chloride as a reactant. More particularly, it will be relatively difficult to remove unreacted methyl chloride from the reaction product stream since the boiling point of methyl chloride (−24° C.) is relatively close to the boiling point of the desired 2,3,3,3-tetrafluoropropene (−28° C.).

The production of 2,3,3,3-tetrafluoropropene by a pyrolysis reaction is also disclosed in U. S. Pat. No. 4,086,407. The process disclosed in this patent has the disadvantage of requiring the use of a relatively complex and uncommon compound, namely, 1-trifluoromethyl-1,2-trifluorcyclobutane, as the starting material for the pyrolysis reaction. Furthermore, like U. S. Pat. No. 2,931,840 described above, the '407 patent does not disclose that the process is effective for the production of 1,3,3,3-tetrafluoropropene.

SUMMARY OF THE INVENTION

Applicants have discovered a process for the synthesis of 1,3,3,3-tetrafluoropropene that overcomes at least the deficiencies of the prior art noted above.

The processes of the present invention according to one embodiment generally comprise (a) reacting a compound of the formula (I) $CF_3X^1$ with a compound of formula (II) $CX^2H=CHX^3$, wherein $X^1$, $X^2$, and $X^3$ are each independently selected from the group consisting of fluorine, chlorine, bromine and iodine, to produce a reaction product comprising a compound of formula (III) $CF_3CH=CHX^3$, wherein $X^3$ is as described above; and (b) when $X^3$ in formula (III) is not fluorine, fluorinating the compound of formula (III) to produce 1,3,3,3-tetrafluoropropene. For the purposes of convenience but not by way of limitation, the processes in accordance with this embodiment are sometimes referred to herein as "the hydrohaolgen addition process."

The present invention according to another embodiment comprises:

(a) providing at least one compound of Formula (I) $R^a—R^0—R^b$, where $R^a$ and $R^b$ are each independently H, F, Cl, Br, I, substituted or unsubstituted one, two or three carbon alkyl, substituted or unsubstituted one or two carbon alkylene bonded also to the other one of $R^a$ or $R^b$ or with a second bond to $R^0$, or —O— bonded also to the other one of $R^a$ or $R^b$, and $R^0$ is $—CF_2—$, $—C_2F_2—$,

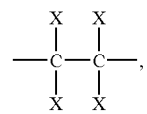

where each x is independently H, F, Cl, Br, I or substituted or unsubstituted one, two or three carbon alkyl, provided that at least two x are F;

and (b) exposing at least one compound of Formula (I) to conditions effective to form 1,3,3,3-tetrafluoropropene ($CF_3CH=CHF$). In certain preferred embodiments, the exposing step comprises exposing said compound(s) to conditions effective to cause pyrolysis of said compound(s), preferably by introducing said compound(s), either together or separately, into a pyrolysis reactor. For the purposes of convenience but not by way of limitation, the processes in accordance with this embodiment are sometimes referred to herein as "the pyrolysis processes."

The present invention is thus directed to processes for the production of $CF_3CH=CFH$ which are amenable to scale up from readily available and relatively inexpensive starting materials.

DETAILED DESCRIPTION OF PREFERRED EMBODIMENTS

The present invention is directed to methods for the production of both the cis- and trans-isomers of 1,3,3,3 tetrafluoro-2-propene, $CF_3CH=CHF$ ("HFC-1234 ze").

For the purposes of convenience, but not by way of limitation, the hydrohalogen addition processes and the pyrolysis processes will be described separately below.

Hydrohalogen Addition Process

The step of reacting a compound of formula (I) with a compound of formula (II) is amenable to a large number of specific processing condition and steps in accordance with the teachings contained herein, and all such variations are within the broad scope of the present invention. It is generally preferred that the reaction step comprises a liquid phase reaction, preferably carried out in a solvent. Suitable solvents include methanol, ethanol, tetrahydrofuran, acetonitrile, dimethylformamide and the like. The temperature of the reaction is preferably from about 5° C. to about 250° C., and more preferably from about 75° C. to about 125° C. It is also generally preferred that the reaction take place in the presence of a catalyst, preferably Pd/C or a mixture of about 1% to about 10% Pd and about 99% to about 90% Cu on activated carbon. The pressure of the reaction is preferably maintained from about 2 psig to about 100 psig. This reaction can in many embodiments be carried out as generally described *Journal of the Chemical Society, Perkin Transactions* 2: *Physical Organic Chemistry* (1999), (11), 2481-2484, which is incorporated herein by reference. In certain embodiments, the reaction can be conducted in an autoclave, with NaOH or the like being added to neutralize the byproduct HCl.

In embodiments in which the reaction step (a) produces a compound of formula (III) wherein $X^3$ in is not fluorine, then the resulting compound is subjected to a fluorination reaction. It is contemplated that numerous variations of fluorination conditions are effective for the purposes of the present invention, and all such conditions are within the broad scope of the invention. It is contemplated that fluorination can take place in either the gas or the liquid phase, although gas phase fluorination is generally preferred. For gas phase fluorination, it is generally preferred to utilize a catalyzed, preferably a Cr-oxide ($Cr_2O_3$) catalyzed, gas-phase fluorination at a temperature of from about 250° C. to about 500° C. in the presence HF, preferably anhydrous HF gas. In certain preferred embodiments, a flow reactor is used for the fluorination reaction. The fluorination reaction generally produces a reaction product comprising 1,3,3,3 tetrafluoro-2-propene.

In certain embodiments, the fluorination reaction may occur substantially simultaneously with the step (a) reaction, for example by conducting the step (a) reaction in the presence of hydrogen fluoride and under the appropriate conditions.

The reacting step (a), together with the fluorinating step (b) when present, preferably produces a reaction product stream which comprises 1,3,3,3-tetrafluoropropene, more preferably comprises a major proportion of 1,3,3,3-tetrafluoropropene, and even more preferably comprises at least about 45% to about 60% 1,3,3,3-tetrafluoropropene.

Any by-products contained in the reaction product stream can be removed to the extent desired by known means, such as distillation etc.

Pyrolysis Processes

The processes in accordance with this embodiment involves reacting, preferably under pyrolytic conditions, one or more compounds to produce tetrafluoropropene, preferably 1,3,3,3-tetrafluoropropene. The reactants preferably comprise one or more compounds of Formula (I) $R^a$—$R^o$—$R^b$, as defined above. Although applicants to not wish to be bound by or to any particular theory of operation, it is believed that the one or more compounds of Formula (I) are capable of producing, under appropriate pyrolytic conditions, a reaction mixture comprising diflurocarbene radicals and difluoroethylene, with vinylidene fluoride being preferred, which are converted, directly or through one or more intermediates, into the preferred tetrafluoropropene, and in particular 1,3,3,3-tetrafluoropropene. Thus, one aspect of the present invention is a process that provides a reaction mixture containing diflurocarbene radicals and difluorethylene (preferably vinylidene fluoride, but also possibly 1,2 difluoroethylene) under conditions effective to produce 1,3, 3,3-tetrafluoropropene. Without being bound by or to theory, it is expected that the pyrolysis reaction involves addition of difluorocarbene ($:CF_2$) to difluoroethylene (preferably vinylidene fluoride ($CF_2=CH_2$)) to form a presumed cyclic intermediate which decomposes to many products, one among such products being $CF_3CH=CFH$. This can be depicted as Scheme 1 below:

Scheme 1

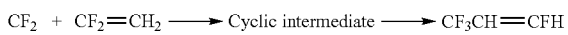

$$CF_2 + CF_2=CH_2 \longrightarrow \text{Cyclic intermediate} \longrightarrow CF_3CH=CFH \quad (1)$$

Another possible reaction scheme (sometimes referred to herein as Scheme 2), without being bound by theory, involves separating fluorine from vinylidene fluoride, leaving a fluorine radical and a —CH=CHF radical, which in turn react in the presence of a difluorcarbene radical to produce CF3CH=CFH. This reaction involves in preferred embodiments is therefore believed to involve insertion of difluorocarbene (:CF2) into a C—F bond.

In yet another alternative mechanism (sometimes referred to herein as Scheme 3), without being bound by theory, it is contemplated that the pyrolysis reaction involves addition of difluorocarbene (:CF2) to vinylidene fluoride CF2=CH2 to form a cyclic intermediate, such as tetraflurorpropane, that decomposes under pyrolysis conditions to produce, among other compounds, CF3CH=CFH. Certain preferred embodiments of this reaction, therefore, are believed to involve insertion of difluorocarbene ($:CF_2$) into a C=C to form a cyclopropane intermediate which then undergoes ring opening to form tetrafluoropropene.

In view of the above, it is contemplated that certain compounds in accordance with Formula (I) are capable of undergoing a thermal cracking process to produce 1,3,3,3-tetrafluoropropene without the inclusion of additional compounds as reactants. For example, processes of the present invention in certain embodiments comprises exposing to thermal cracking conditions tetrafluorocyclopropane, that is, a compound of Formula (I) $R^a$—$R^o$—$R^b$, wherein $R^o$ is —$CF_2$—, $R^a$ is a difluorine substituted one carbon alkylene bonded also $R^b$, and $R^b$ is an unsubstituted one carbon alkylene bonded also $R^a$. More particularly, such cyclic compounds, such as preferably 1,1,2,2 tetrafluorcyclopropane, are capable of undergoing a thermal cracking reaction to produce 1,3,3,3-tetrafluoropropene by way of either mechanism described above. Without being bound by theory, it is believed that under appropriate pyrolysis reaction conditions such cyclic compounds produce diflurocarbene radicals and vinylidene fluoride, which in turn react in accordance with Scheme 1 above to produce 1,3,3,3-tetrafluoropropene. Alternatively or supplementary, such cyclic compound provides the structure of the intermediate in Scheme 2 above, which thereafter reacts, with or without additional intermediates, to form 1,3,3,3-tetrafluoropropene.

In other embodiments, the present methods comprise co-pyrolzing two compounds, preferably two compounds in accordance with Formula (I), wherein the first compound is capable of producing under reaction conditions diflurocarbene radicals and the second compound is capable of producing under reaction conditions vinylidene fluoride. It is believed that those skilled in the art will be able to readily identify, in view of the teachings contained herein, a large number of compounds capable of producing diflurocarbene radicals, and all such compounds are with the broad scope of the present invention. Likewise, it is believed that those skilled in the art will be able to readily identify, in view of the teachings contained herein, a large number of compounds capable of producing vinylidene fluoride, and all such compounds are also with the end the broad scope of the present invention. Some preferred compounds capable of producing diflurocarbene radicals include: $CF_2HCl$ (HCFC-22, bp −41 C. °), hexafluoropropene epoxide, tetrafluoroethylene, and perfluorocyclopropane. Examples of some preferred compounds capable of producing or providing vinylidene fluoride include: $CF_2ClCH_3$ (HCFC-142b) vinylidene fluoride, $CF_3CH_3$, and $CF_2HCH_2Cl$.

In certain co-pyrolysis embodiments, it is preferred to co-pyrolyze at least a first compound of Formula (I) (referred to hereinafter as a Formula $I^1$ Compounds) where $R^0$ is —$CF_2$— and a second compound of Formula (I) (referred to hereinafter as a Formula $I^2$ Compound) where
$R^0$ is —$C_2F_2$— or

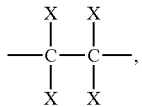

where each x is independently H, F, Cl, Br, I or substituted or unsubstituted one, two or three carbon alkyl, provided that at least two x are F.

Applicants believe, without being bound, that the Formula ($I^1$) compounds provide difluorocarbene radicals under pyrolytic conditions and that the Formula ($I^2$) compounds produce or provide vinylidene fluoride under pyrolytic conditions. Examples of preferred Formula ($I^1$) compounds include $CF_2HCl$ (HCFC-22, bp −41 C), hexafluoropropene epoxide, tetrafluoroethylene, and perfluorocyclopropane. Examples of preferred Formula ($I^2$) compounds include $CF_2ClCH_3$ (HCFC-142b) vinylidene fluoride, $CF_3CH_3$, and $CF_2HCH_2Cl$. For certain preferred embodiments it is preferred that approximately one mole of the Formula ($I^2$) compounds, such as $CF_2ClCH_3$, $CF_3CH_3$, and $CF_2HCH_2Cl$ (or combinations thereof) are copyrolyzed with about 0.2 to about 1.5 mole of Formula ($I^1$) compounds.

In certain embodiments it is preferred to use about one mole of $CHF_2Cl$ or hexafluoropropene oxide or combinations thereof per mole of Formula ($I^2$) compounds. In other embodiments, it is preferred to use about ½ mole of $CF_2=CF_2$ per mole of Formula ($I^2$) compounds, or about ⅓ mole of perfluorocyclopropane per mole of Formula ($I^2$) compound.

It is contemplated that, in view of the teachings contained herein, persons skilled in the art will be capable of utilizing numerous and varied reaction conditions with good effect for the pyrolysis reaction of the present invention, and all such conditions are within the broad scope of present invention. As the term is used herein, "pyrolysis" and like terms refer to exposing one or more compounds to conditions effective to achieve thermal cracking of the compound. In preferred embodiments, the pyrolysis reaction comprises exposing reactants, and preferably one or more compounds in accordance with Formula (I), to temperatures of from about 670° C. to about 1000° C., and even more preferably of from about 700° C. to about 900° C. at contact times effective to produce the desired tetrafluoropropene, particularly, 1,3,3,3-tetrafluoropropene. In preferred embodiments, the contact time is from about 0.5 seconds to about 10 seconds, and even more preferably from about 0.5 seconds to about 3 seconds. As is known to those skilled in the art, the temperature and contact time of the reactants can be varied by making adjustments to process conditions such as reactant feed rate, reactor vessel pressure, reactor volume, and the like.

It is contemplated that the reaction product will contain, in addition to the desired 1,3,3,3-tetrafluoropropene, unreacted starting materials and byproducts, and accordingly downstream processing will generally include unit operations such as scrubbing (to remove acid gases such as HCl) and distillation to obtain a relatively purified product. More particularly, the product mixture is expected to contain substantial amounts of CF3CF=CH2 and CF3CH=CHF along with varying amounts of fluorinated propenes and ethylenes, such as CF2HCF=CF2, CF2=CH2, and CF2=CF2. In certain preferred embodiments, the fluorinated ethylenes can be recycled into the reactor. CF2HCH=CF2 can be isomerized to CF3CH=CHF. Typical yields of the desired product, CF3CH=CFH preferably range form about 10% to 25%.

The reaction of the present invention can occur in a large number of environments, and all such environments are within the broad scope of the present invention. In preferred embodiments, the pyrolysis reaction of the present invention occurs in a reaction vessel, preferably a tubular reaction vessel. Although it is contemplated that numerous materials and constructions are available for the formation of such a reaction vessel, it is generally preferred that the tubular vessel is formed from noble metals, such as platinum and silver. Nickel may also be used as a material of construction in preferred reactors. In operation of such preferred reactors, the reaction vessel is contained with a furnace which is heated to produce the desired pyrolysis conditions. Any known and available heat source can be used, including electrical and gas-fired furnaces.

The following examples are given as specific illustrations of the invention. It should be noted that, however, that the invention is not limited to the specific details set forth in the examples. All isomers (cis and trans) of $CF_3CH=CFH$ are within the scope of the invention.

EXAMPLES

Example 1

Synthesis of CF3CH=CFH via Reductive Coupling $CF_3Br$ (0.25 mol) is reacted in 5 mol methanol with 0.25 mol of ClHC=CHF at a temperature of from about 15° C. to about 100° C. in the presence of about 0.005 mol of Pd/C or a mixture of about 1% to about 10% Pd and about 99% to about 90% Cu on activated carbon in an high pressure autoclave. 0.3 mol $H_2$ gas, 0.6 mol NaOH or $Na_2CO_3$, and 0.001 mol of Tetrabutylammonium bromide are also added in to the reactor. After from about 6 to about 20 hrs of stirring at about 25° C. to about 150° C., the autoclave is cooled down and the reaction product is obtained in the form of overhead gases. The reaction product comprises $CF_3CH=CHF$ in yield of about 5-10%.

Examples 2-14

The reactor used in following examples will consist of a platinum-lined tube 6 mm ID.×24 inches heated in an 8 inch (heated area 5. 5 inch) electric furnace. The product gas is analyzed by GC-MS.

Example 2

A mixture of 100 mL/min $CHF_2Cl$ and 100 mL/min $CF_2ClCH_3$ is passed through the reactor described above at a contact time of about 1.19 seconds and at a temperature of about 700° C. to about 900° C. The gaseous reaction products are scrubbed free of by-product HCl and dried and analyzed by GC-MS. The scrubbed and dried product stream is found to contain 15 mole percent of tetrafluoropropenes.

Example 3

A mixture of 100 mL/min $CHF_2Cl$ and 100 mL/min $CF_2=CH_2$ is passed through the reactor described above at a contact time of about 1.19 seconds and at a temperature of about 700° C. to about 900° C. The gaseous reaction products are scrubbed free of by-product HCl and dried and analyzed by GC-MS. The scrubbed and dried product stream is found to contain 10 mole percent of tetrafluoropropenes.

Example 4

A mixture of 100 mL/min $CHF_2Cl$ and 100 mL/min $CF_3CH_3$ is passed through the reactor described above at a contact time of about 1.19 seconds and at a temperature of about 700° C. to about 900° C. The gaseous reaction products are scrubbed free of by-product HCl and dried and analyzed by GC-MS. The scrubbed and dried product stream is found to contain 20 mole percent of tetrafluoropropenes.

Example 5

A mixture of 100 mL/min $CHF_2Cl$ and 100 mL/min $CHF_2CH_2Cl$ is passed through the reactor described above at a contact time of about 1.19 seconds and at a temperature of about 700° C. to about 900° C. The gaseous reaction products are scrubbed free of by-product HCl and dried and analyzed by GC-MS. The scrubbed and dried product stream is found to contain 15 mole percent of tetrafluoropropenes.

Example 6

A mixture of 50 mL/min $CF_2=CF_2$ and 100 mL/min $CF_2=CH_2$ is passed through the reactor described above at a contact time of about 1.19 seconds and at a temperature of about 700° C. to about 900° C. The gaseous reaction products are scrubbed free of by-product HCl and dried and analyzed by GC-MS. The scrubbed and dried product stream is found to contain 13 mole percent of tetrafluoropropenes.

Example 7

A mixture of 50 mL/min $CF_2=CF2$ 100 mL/min $CF_2ClCH_3$ is is passed through the reactor described above at a contact time of about 1.19 seconds and at a temperature of about 700° C. to about 900° C. The gaseous reaction products are scrubbed free of by-product HCl and dried and analyzed by GC-MS. The scrubbed and dried product stream is found to contain 15 mole percent of tetrafluoropropenes.

Example 8

A mixture of 100 mL/min perfluoropropene oxide and 100 mL/min $CF_2=CH_2$ is passed through the reactor described above at a contact time of about 1.19 seconds and at a temperature of about 700° C. to about 900° C. The gaseous reaction products are scrubbed free of by-product HCl and dried and analyzed by GC-MS. The scrubbed and dried product stream is found to contain 15 mole percent of tetrafluoropropenes.

Example 9

A mixture of 100 mL/min perfluoropropene oxide and 100 mL/min $CF_2ClCH_3$ is passed through the reactor described above at a contact time of about 1.19 seconds and at a temperature of about 700° C. to about 900° C. The gaseous reaction products are scrubbed free of by-product HCl and dried and analyzed by GC-MS. The scrubbed and dried product stream is found to contain 16 mole percent of tetrafluoropropenes.

Example 10

A mixture of 100 mL/min perfluoropropene oxide and 100 mL/min $CF_2HCH_2Cl$ is passed through the reactor described above at a contact time of about 1.19 seconds and at a temperature of about 700° C. to about 900° C. The gaseous reaction products are scrubbed free of by-product HCl and dried and analyzed by GC-MS. The scrubbed and dried product stream is found to contain 15 mole percent of tetrafluoropropenes.

Example 11

A mixture of 50 mL/min perfluorocyclopropane and 150 mL/min $CF_2ClCH_3$ is passed through the reactor described above at a contact time of about 1.19 seconds and at a temperature of about 700° C. to about 900° C. The gaseous reaction products are scrubbed free of by-product HCl and dried and analyzed by GC-MS. The scrubbed and dried product stream is found to contain 14 mole percent of tetrafluoropropenes.

Example 12

A mixture of 50 mL/min perfluorocyclopropane and 150 mL/min $CF_2=CH_2$ is passed through the reactor described above at a contact time of about 1.19 seconds and at a temperature of about 700° C. to about 900° C. The gaseous reaction products are scrubbed free of by-product HCl and dried and analyzed by GC-MS. The scrubbed and dried product stream is found to contain 18 mole percent of tetrafluoropropenes.

Example 13

A mixture of 50 mL/min perfluorocyclopropane and 150 mL/min $CF_2HCH_2Cl$ is passed through the reactor described above at a contact time of about 1.19 seconds and at a temperature of about 700° C. to about 900° C. The gaseous reaction products are scrubbed free of by-product HCl and dried and analyzed by GC-MS. The scrubbed and dried product stream is found to contain 15 mole percent of tetrafluoropropenes.

Example 14

200 mL/min 1-H,1-H-tetrafluorocyclopropane is passed through the reactor described above at a contact time of about 1.19 seconds and at a temperature of about 700° C. to about 900° C. The gaseous reaction products are scrubbed free of by-product HCl and dried and analyzed by GC-MS. The scrubbed and dried product stream is found to contain 15 mole percent of tetrafluoropropenes.

What is claimed is:

1. A process for the synthesis of 1,3,3,3 tetrafluoropropene comprising:
    a) reacting a compound of the formula (I) $CF_3X^1$ with a compound of formula (II) $CX^2H{=}CHX^3$, wherein $X^1$, $X^2$, and $X^3$ are each independently selected from the group consisting of fluorine, chlorine, bromine and iodine, to produce a reaction product comprising a compound of formula (III) $CF_3CH{=}CHX^3$, wherein $X^3$ is as described above; and
    b) when $X^3$ in formula (III) is not fluorine, fluorinating the compound of formula (III) to produce 1,3,3,3-tetrafluoropropene.

2. The process of claim 1 wherein said reacting step (a) comprises reacting a compound of formula (I) and a compound of formula (II) in a liquid phase reactor.

3. The process of claim 2 wherein said reactor includes catalyst.

4. The process of claim 1 wherein $X^1$ is Br, $X^2$ is Cl and $X^3$ is F.

* * * * *